United States Patent [19]

Silverstein et al.

[11] Patent Number: 5,247,938

[45] Date of Patent: Sep. 28, 1993

[54] METHOD AND APPARATUS FOR DETERMINING THE MOTILITY OF A REGION IN THE HUMAN BODY

[75] Inventors: Fred E. Silverstein, Seattle; Roy W. Martin, Redmond; Michael B. Kimmey, Seattle; Michael D. Schuffler, Mercer Island; Andrew H. Proctor, Duvall; Geoffrey C. Jiranek, Seattle, all of Wash.

[73] Assignee: University of Washington, Seattle, Wash.

[21] Appl. No.: 463,548

[22] Filed: Jan. 11, 1990

[51] Int. Cl.$^5$ ............................................. A61B 8/08
[52] U.S. Cl. ..................... 128/662.030; 128/662.060; 128/748
[58] Field of Search ............... 128/662.06, 662.03, 128/662.04, 660.03, 713, 631, 748, 661.09, 660.03, 662.06

[56] References Cited

U.S. PATENT DOCUMENTS

| | | |
|---|---|---|
| 3,124,132 | 3/1964 | Sullivan et al. |
| 3,661,146 | 5/1972 | Peronneau et al. |
| 3,921,622 | 11/1975 | Cole. |
| 3,938,502 | 2/1976 | Bom .............................. 128/662.06 |
| 3,955,560 | 5/1976 | Stein et al. |
| 3,977,247 | 8/1976 | Hassler. |
| 4,156,304 | 5/1979 | Lee .............................. 128/660.04 |
| 4,273,111 | 6/1981 | Tsukaya ......................... 128/6 |
| 4,313,443 | 2/1982 | Lund. |
| 4,327,738 | 5/1982 | Green et al. ................... 128/662.06 |
| 4,354,500 | 10/1982 | Colley et al. .................. 128/661.07 |
| 4,354,501 | 10/1982 | Colley et al. .................. 128/662.06 |
| 4,354,502 | 10/1982 | Colley et al. .................. 128/662.06 |
| 4,355,463 | 10/1982 | Burns. |

(List continued on next page.)

FOREIGN PATENT DOCUMENTS

| | | |
|---|---|---|
| 0129878 | 3/1984 | European Pat. Off. |
| 0270733A1 | 6/1988 | European Pat. Off. |
| 2585944 | 7/1987 | France. |
| 217689 | 6/1988 | France. |

OTHER PUBLICATIONS

*A Venous Pulse Doppler Catheter-Tip Flowmeter for Measuring Arterial Blood Velocity, Flow and Diameter in Deep Arteries;* R. C.Nealeigh and C. W. Miller ISA Transactions, 1976, vol. 15, No. 1, pp. 84–87.

*Doppler Measurement of Myocardial Thickening with a Single Epicardial Transducer* Craig J. Hartley et al., American Journal of Physiology, 1983, vol. 245, pp. H1066–H1072.

*Continuous Monitoring of Cardiac Output Postoperatively Using an Implantable Doppler Probe* J. L. Svennevig et al., Scand J. Thor Cardiovasc Surg., vol. 20, 1986, pp. 145–149.

*Perioperative Assessment of Segmental Left Ventricular Function in Man* Ronald C. Hill, M.D. et al., Arch Surg., May 1980, vol. 115, pp. 609–614.

Primary Examiner—Francis Jaworski
Assistant Examiner—Kevin Pontius
Attorney, Agent, or Firm—Seed and Berry

[57] ABSTRACT

Devices are described which can be used to study the physiological function of the intestinal wall. These devices include an ultrasonic transducer that can be attached to a region of the intestinal wall. The transducer interrogates the wall and echoes are obtained from the different wall layers. The echoes are processed to produce an M-mode display of the wall. This allows monitoring how the wall changes with time. For example, as the wall contracts the muscle layer thickens and this action may be observed with the device. Other sensors and electrodes can be combined with this probe to correlate various physiological action. Finally, several such probes can be combined into a common introducible probe but which will monitor several regions along the intestinal wall. The major advantage of the disclosed device is that it provides a measurement of intestinal motility previously unattainable and it is introducible by endoscopy. This makes it a suitable tool for studying patient disease.

21 Claims, 10 Drawing Sheets

U.S. PATENT DOCUMENTS

| | | | |
|---|---|---|---|
| 4,355,643 | 10/1982 | Laughlin et al. | 128/662.04 |
| 4,375,818 | 3/1983 | Suwaki et al. | 128/662.06 |
| 4,391,282 | 7/1983 | Ando et al. | 128/662.06 |
| 4,398,540 | 8/1983 | Takemura et al. | 128/661.004 |
| 4,408,612 | 10/1983 | Utsugi | 128/662.06 |
| 4,417,583 | 11/1983 | Bechai et al. | 128/662.06 |
| 4,419,999 | 12/1983 | May, Jr. et al. | |
| 4,424,813 | 1/1984 | Havlice et al. | 128/660.04 |
| 4,442,844 | 4/1984 | Navach . | |
| 4,462,408 | 7/1984 | Silverstein et al. | 128/662.06 |
| 4,541,433 | 9/1985 | Baudino . | |
| 4,630,612 | 12/1986 | Uchida et al. | 128/661.09 X |
| 4,742,829 | 5/1988 | Law et al. | 128/662.05 |
| 4,744,368 | 5/1988 | Young et al. . | |
| 4,823,800 | 4/1989 | Compos . | |
| 4,841,977 | 6/1989 | Griffith et al. | 128/660.003 |
| 4,846,191 | 7/1989 | Brockway et al. | 128/748 |
| 4,915,113 | 4/1990 | Holman | 128/691 |
| 4,926,875 | 5/1990 | Rabinovitz et al. | 128/691 |
| 4,947,854 | 8/1990 | Rabinovitz et al. | 128/662.004 |

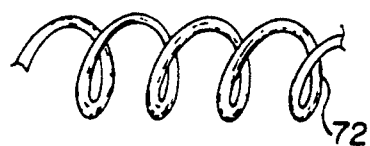
FIG. 6A
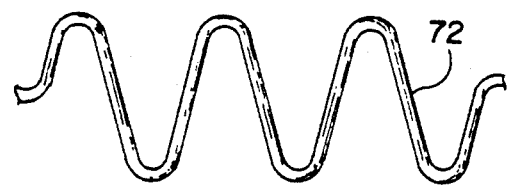
FIG. 6B
FIG. 6C
FIG. 7
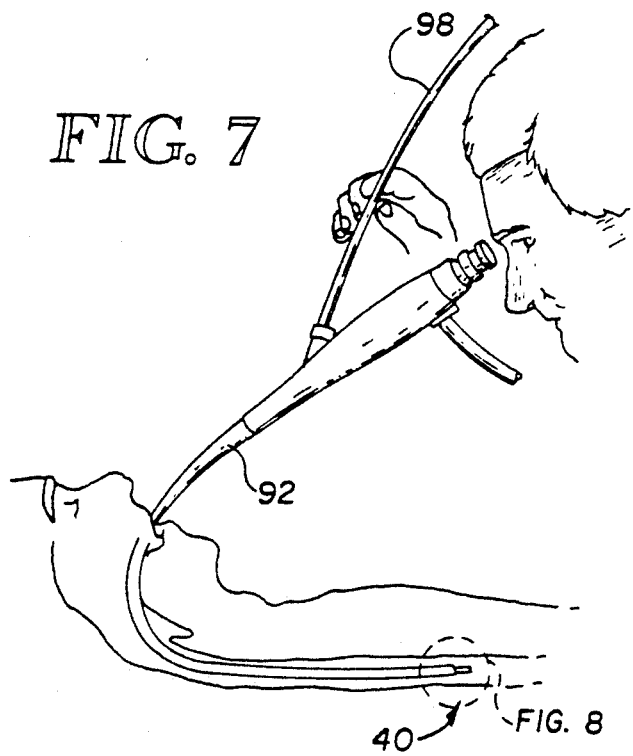

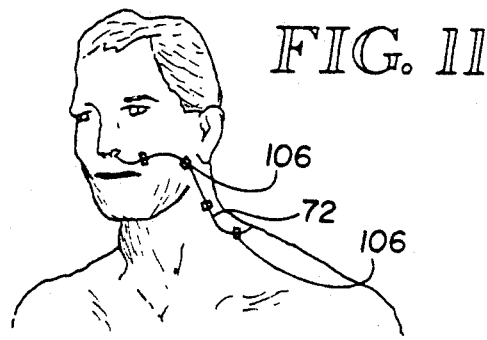
FIG. 11
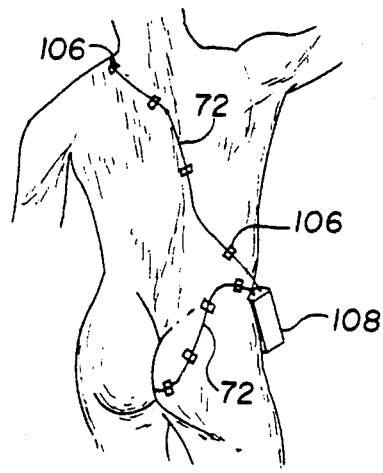
FIG. 12
FIG. 13
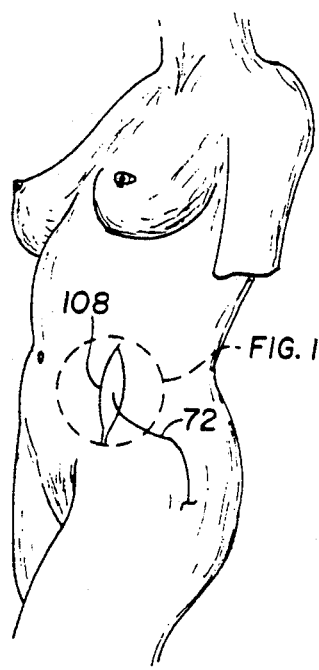
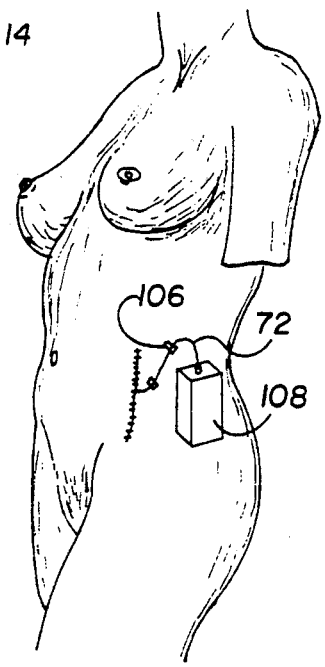
FIG. 15
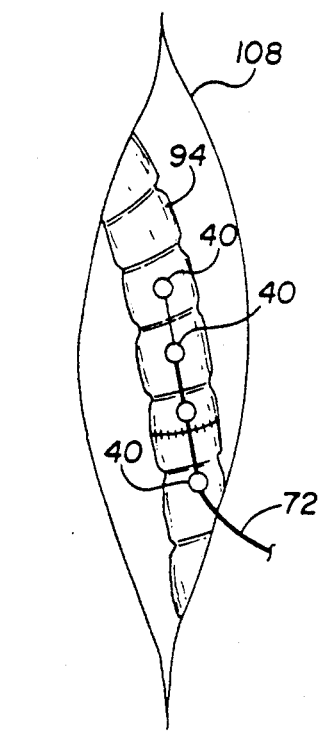
FIG. 14

METHOD AND APPARATUS FOR DETERMINING THE MOTILITY OF A REGION IN THE HUMAN BODY

This invention was made with government support under Grant No. DK 34814 awarded by the National Institutes of Health. The government has certain rights in the invention.

DESCRIPTION

1. Technical Field

This invention relates to a method and apparatus for determining the motility of a region of the human body, and more particularly, to a probe coupled to a wall of the digestive tract for monitoring movement of the wall.

2. Background of the Invention

Disorders of the digestive system, and particularly of the gastrointestinal tract, are common. Many people are affected with disorders which include chest pain, difficulties with emptying of the stomach, chronic diarrhea, abnormalities of the colon, or abdominal cramp pain. The exact cause of the difficulty is often not discoverable using today's technology.

Presently, evaluation of the intestinal tract motility function is extremely difficult, if possible. If monitoring movement of the digestive tract is desired, one or more of the following techniques are currently used: (1) X-ray studies in which barium is given and the progress of the barium through the intestine is monitored with an X ray; (2) manometry studies in which pressure sensors are placed within a section of the intestine to sense pressure changes in the wall of the intestine at the location under study; (3) a balloon catheter study in which a balloon is inflated within the gastrointestinal tract to sense pressure and shape changes; (4) radionuclide studies performed by gamma cameras to follow quantitatively the emptying of radioactive material in both solids and liquids within the organ to be studied; (5) electrophysiological studies in which electrodes are placed within the mucosa of the intestinal wall to detect changes in electrical activity in an attempt to correlate them with the motility function. Each of the prior art techniques has significant limitations and drawbacks. Further, despite the prior art techniques, there are still many unanswered questions regarding the movement of the digestive tract over both short and long periods of time.

One present problem is the difficulty of following the movement of the intestinal wall while the event is occurring in vivo using the prior art devices. The prior art devices often cause a change in the digestive tract in which the measurement is taking place. For example, inflating a balloon within digestive tract to measure the movement of the tract causes a change in the motility of the local region being measured.

SUMMARY OF THE INVENTION

It is therefore an object of the invention to provide a method for measuring movement of walls of the digestive tract over time.

It is a further object of the invention to provide an apparatus for measuring movement in walls of the digestive tract over short and long periods of time.

These and other objects of the invention are accomplished by providing a probe which is attachable to a wall of the digestive tract. The probe includes an ultrasonic transducer which operates at frequencies sufficiently high to distinguish individual features within the wall, e.g., approximately 20 megahertz. Pressure sensors, electromyography sensors, tension sensors, and the like may also be included within the probe. The probe transmits pulses of ultrasonic energy into the wall over a selected interval of time. The ultrasonic energy reflected from individual layers within the wall is processed and digitally encoded. A plot is produced displaying the thickness of each layer and the change in thickness of the layers over time. A plurality of probes may extend longitudinally along the digestive tract. The plots from each probe may be compared to each other to determine movement of one region of the wall with respect to another region of the wall over time.

BRIEF DESCRIPTION OF THE DRAWINGS

FIGS. 6a–6c illustrate a plurality of alternative embodiments of service loops between individual probes.

FIG. 7 is a side elevational view of a first embodiment of probe placement using an endoscope.

FIG. 11 is an isometric view of the probe output wire extending from the digestive tract and out of the nasal passage, for coupling to a controller.

FIG. 12 is a rear isometric view of coupling wires from probes extending from the digestive tract out of the nasal passage and rectum, respectively, and coupled to an ambulatory control device.

FIG. 13 is a front elevational view of the probe placement on an organ of the body during surgery.

FIG. 14 is an enlarged view of the surgically placed probes of FIG. 13.

FIG. 15 is a front elevational view of the probes of FIG. 13 coupled to an ambulatory device through a service loop exiting from a surgical opening in the body.

DETAILED DESCRIPTION OF THE INVENTION

Figure 1:
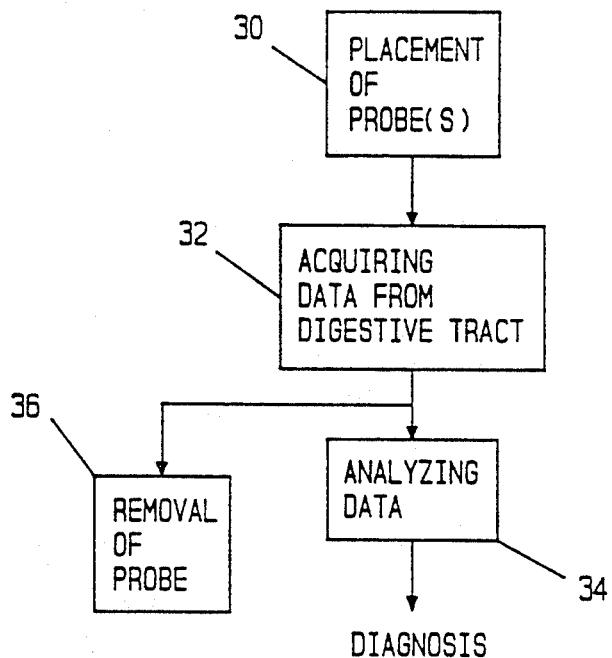
FIG. 1 is a flow diagram of the method of carrying out the invention.

FIG. 1 is a flow chart of the method for carrying out the invention. The ultrasonic digestive tract motility diagnostic system includes four processing steps: (1) the step 30 of placing the probes within the patient's body; (2) the step 32 of acquiring data from the region of the digestive tract of interest; (3) the step 34 of analyzing the data acquired from the digestive tract; and (4) the step 36 of removing the probes, which may occur after the data has been analyzed or, alternatively, may occur prior to analysis of the data. A diagnosis 38 follows the processing steps. Each of the four steps is described in more detail herein. An apparatus for carrying out the four steps is also described.

Figure 3:
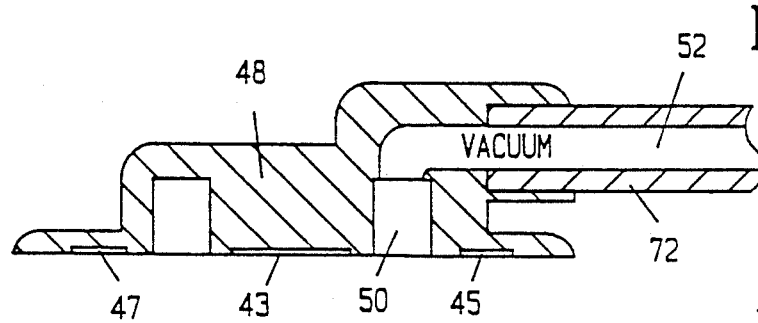
FIG. 3 is a cross-sectional view taken along lines 3—3 of FIG. 2.
Figure 2:
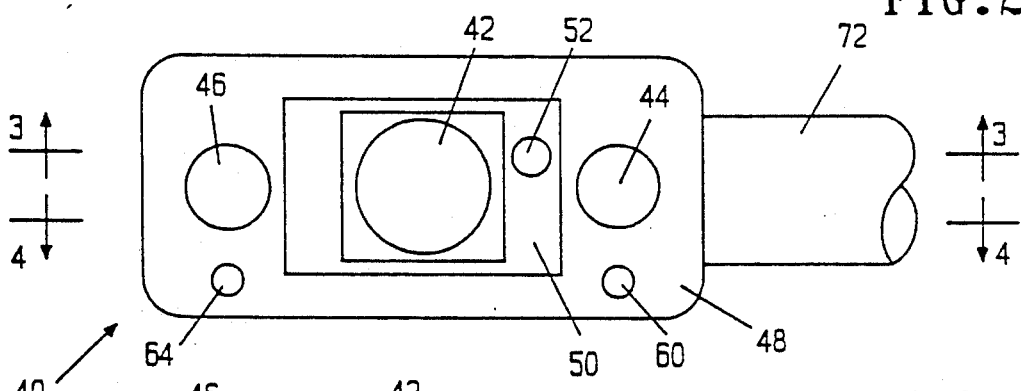
FIG. 2 is a bottom elevational view of a single probe.
Figure 4:
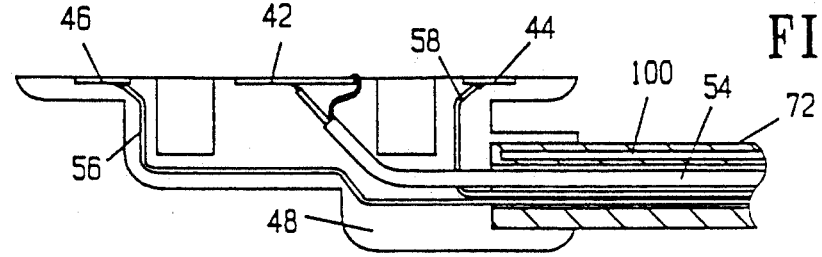
FIG. 4 is a cross-sectional view taken along lines 4—4 of FIG. 2.

FIGS. 2-4 illustrate a single probe 40. The probe 40 includes a housing 48, an ultrasonic transducer 42, electrodes 44 and 46 and sensors 60 and 64. A chamber 50 extends circumferentially within the housing 48. A tubing 52 is coupled to the chamber 50 for evacuating air therefrom to create suction for attaching the probe to the wall. The chamber 50 and tubing 52 may also be a biopsy channel to collect fluids and tissue samples, administer fluids or the like.

The housing 48 includes recesses 43, 45, and 47 into which the ultrasonic transducer 42 and electrodes 44 and 46, respectively, are positioned. The probe housing 48 is constructed to ensure that the ultrasonic transducer 42 and other sensors are appropriately positioned with respect to the region being measured to ensure proper coupling and accurate measurement for the particular sensor.

The probe 40 is coupled to external equipment via service loop 72. The service loop 72 includes a cable 54 for coupling the transducer 42 to a control circuit 120 (shown in FIG. 18). The electrodes 44 and 46 are coupled via wires 56 and 58, respectively, to a control circuit 132 (shown in FIG. 18). A common ground may be used for the electrodes and transducer if desired. Service loop 72 includes a removable stiffening rod 100.

The electrodes 44 and 46 are useful for measuring other parameters not measured by the ultrasonic transducer 42. For example, the electrodes 44 and 46 may measure physiological functions such as pH, electromyography, or the like. The electrodes 44 and 46 may be piezoelectric elements, low resistance electrodes, dual electrodes operating as a pair or some other sensors. Additional sensors 60 and 64 may be included within the probe 40 if desired. The sensor 60 may be a force transducer with a spring placed in series to permit measurement of isometric and isotonic muscle contractions. Sensor 64 is a manometry lumen or pressure transducer to measure fluid (liquid or gas) pressure generated within the digestive tract. Muscle pressure may also be measured. Numerous other sensors may be included in the probe 40 in place of or in addition to sensors 60 and 64 if desired. Alternatively, the probe 40 may include only the transducer 42 and have dimensions approximately equal to those of the transducer itself.

Use of a probe 40 capable of performing multiple functions allows obtaining measurements of many measurands simultaneously and at the same region so that it will be possible to correlate the data. For example, lumenal pressure may be correlated with electrophysiological data and wall thickening due to a contraction as measured by M mode. Alternatively, M-mode ultrasonic measurement of wall thickening may be correlated with the electromyography. Simultaneous assessment of circular and longitudinal muscle activity is possible with probes 40. Circular muscle contraction, as evidence by increased tension and decreased length, may be measured. Additionally, isolated regions may be simultaneously measured with respect to their longitudinal muscle tension, circular muscle tension, length, and other parameters.

The ultrasonic transducer 42 is preferably miniaturized and capable of high-frequency operation. In one embodiment, the ultrasonic transducer is a single circular element 1 millimeter in diameter and weighing 0.2 gram, about the size of a pin head. The frequency of the transducer is selected to be sufficiently high to permit individual layers of the walls of the digestive tract to be identified while being sufficiently low to pass completely through the wall, though some energy is reflected at each interface. A frequency of approximately 20 megahertz has been found suitable, though other frequencies, for example, 15 to 25 megahertz, may also be suitable. When emitting ultrasonic energy at 20 megahertz, the element provides an axial resolution of 0.2 millimeter, sufficient to resolve individual layers within a wall of the digestive tract.

The probe 40 is sufficiently small and lightweight that they do not alter the shape and function of the digestive tract in which they are placed. In one embodiment, the probe 40 is approximately 3 millimeters wide and 6.6 millimeters long, with a height of approximately 2 millimeters. The entire probe is sufficiently lightweight that localized pressure or sagging of the wall of the digestive tract does not occur. Preferably, the probe 40 has a weight in the range of 1 gram, but the weight may vary based on the number and type of measuring devices included in the probe, and the like.

The probe 40 may be coupled to the wall of the digestive tract by a variety of techniques. The probe 40 preferably adheres to the mucosa of the intestinal tract lumen. The adherence may be accomplished either with a clip, a temporary glue (such as cyanoacrylate), or a suction chamber 50 which gently attaches to the mucosa, as shown in the embodiment of FIGS. 2-4. An example of a suitable suction cup for use with the ultrasonic transducer of the invention is illustrated in U.S. Pat. No. 4,355,643. An alternative technique is suturing of the probe to the intestinal wall.

Figure 22A:
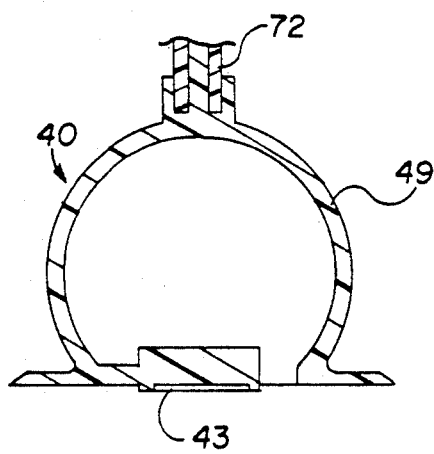
FIGS. 22a and 22b are side elevational views of a suction device for coupling the probe to the wall.
Figure 22B:
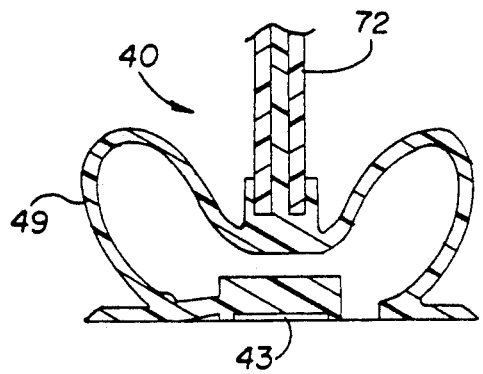

FIGS. 22a and 22b illustrate one technique for coupling the probe head 40 with suction without use of a vacuum tubing 52. A resiliently depressible membrane 49 is coupled to the probe 40. Depressing the membrane 49 creates a suction force as the membrane 49 recovers, to clamp the probe 40 to the wall of the intestine. The service loop 72 need not include a vacuum lumen 52 if the probe includes membrane 49 or is coupled by adhesive or some other method.

Figure 5A:
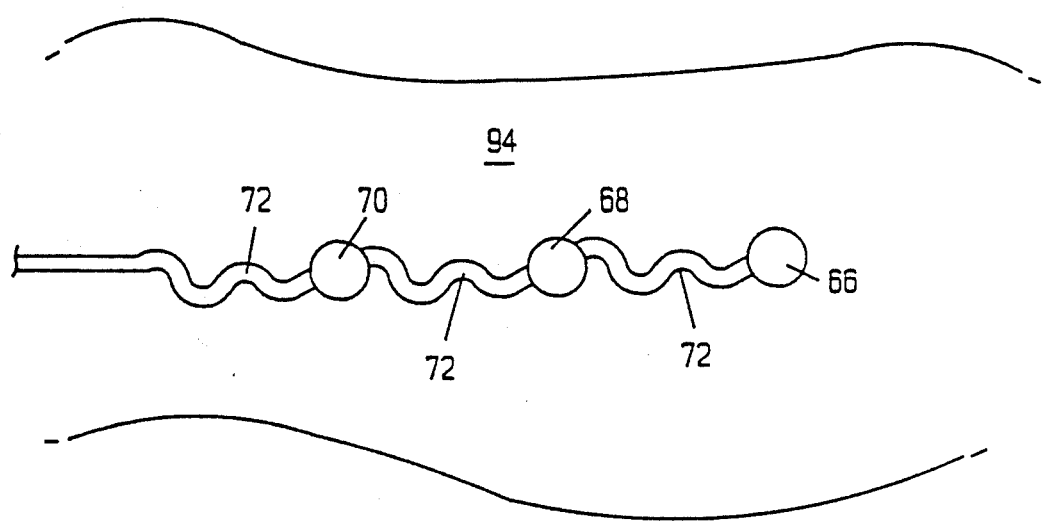
FIGS. 5a and 5b are schematic views of alternative embodiments of a plurality of probes coupled to a wall of the digestive tract.
Figure 5B:
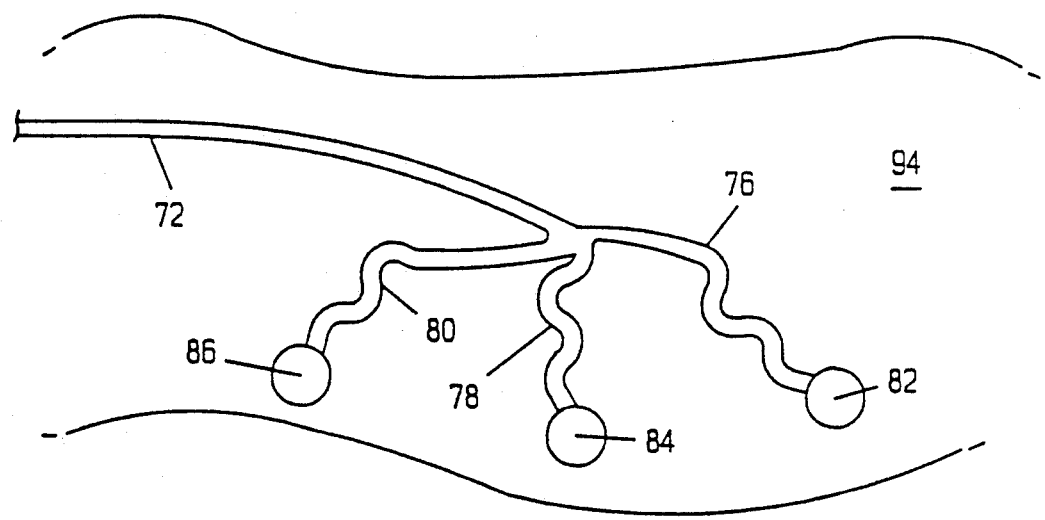

FIGS. 5a and 5b illustrate a plurality of probes coupled together, longitudinally spaced from each other along the digestive tract. In FIG. 5a, probes 66, 68 and 70 are longitudinally spaced series along the digestive tract. A service loop 72 extends in between the probes and between the probes and the external control equipment. Alternatively, a shown in FIG. 5b, the probes may be coupled to a main service loop 72 having individual service loops 76, 78, and 80 in parallel. The service loops 76, 78, and 80 may perform identical functions and have similar couplings therein such that each of the respective probes 82, 84, and 86, coupled in parallel, perform the same function. Alternatively, each of the service loops 76, 78, and 80 may contain different devices to permit each of the respective probes 82, 84, and 86 to perform different functions and measure different physiological parameters. The probes may be spaced circumferentially around the digestive tract rather than longitudinally, if desired, depending upon the region of interest and the physiological parameters being monitored. The service loop is constructed to permit it to perform the desired function without interfering in the physiological parameter being measured.

The service loop 72 may include only cable 4 or, in one embodiment, includes wires 56, 58, lumen 52 and removable rod 100, as shown in FIGS. 2-4. The service loop 72 is flexible to permit the probe 40 to move freely with the wall. As illustrated in FIGS. 5a and 5b, the service loop between the individual probes is sufficiently flexible that the probes may move independent of each other. The service loop is sufficiently lightweight and thin to not affect the functioning of the digestive tract. In one embodiment, the service loop includes the transducer cable 54 and is less than 0.5 millimeter in diameter. In other embodiments, the service loop 72 is sized to carry additional wires and has the described lumens but remains sufficiently small to not interfere with the functioning of the organ whose properties are being measured.

FIGS. 6a-6c illustrate possible configurations of the service loop 72. As illustrated in FIG. 6a, the service loop may be a coil similar to a telephone cord. Alternatively, the loop 72 may have a flat sinusoidal type of configuration, as shown in FIG. 6b. A flat triangle waveform type of configuration, as illustrated in FIG. 6c, may also be used. Each type of service loop 72 is constructed to have a low-force spring action so that it retracts when no force is on it and is easily displaced as the probe 40 moves with the wall of the digestive tract during a contraction.

Figure 8:
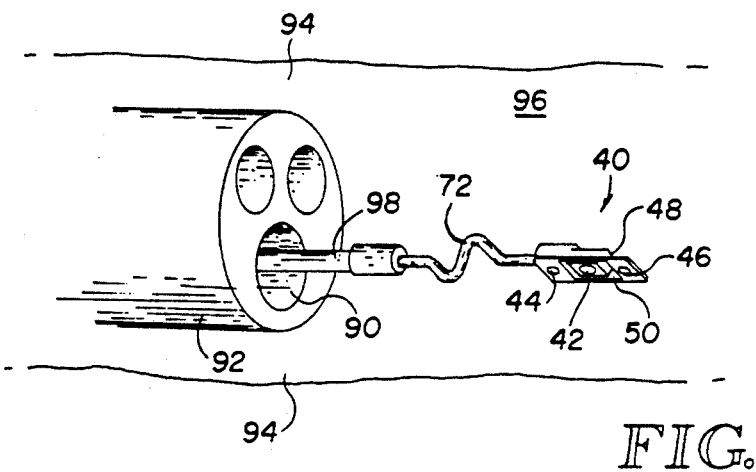
FIG. 8 is an enlarged isometric view of the probe while being placed within the digestive tract taken from FIG. 7.

FIGS. 7-10 illustrate techniques for placing the probe within the digestive tract. As best illustrated in FIG. 8, the probe 40 is introducible through a channel 90 of an endoscope 92. The endoscopist observes the position of the tip of the endoscope 92 and the probe 40 in the intestine lumen 96. The endoscopist guides the placement of the probe 40 by moving the rigid shaft 98, coupled to the service loop 72, within the channel 90. The endoscopist maneuvers the probe 40 until it comes in contact with the desired region of the digestive wall 94. The probe 40 is then attached by activating the suction in the probe, gluing, or some other method, as previously discussed.

To aid in placing the probe 40 within the intestinal lumen 96, the service loop 72 may include a rigid removable rod 100, shown in FIG. 4. The rod 100 may be a relatively stiff wire extending through a lumen along the length of the service loop 72 to the probe 40 for holding the service loop 72 relatively rigid during placement. The rigid rod 100 extending through the service loop 72 permits the probe to be advanced through the intestinal lumen by pushing without the service loop 72 folding over on itself. After the probe 40 is coupled to the intestinal wall 94, the rod 100 is removable from the service loop 72 to permit the service loop 72 to be flexible relative to the probe.

Once the probe is properly attached to the wall, the endoscope 92 is withdrawn from the mouth of the patient and the service loop 72 is allowed to be pulled out of the endoscope channel 90 in a retrograde fashion while the probe 40 remains attached to the intestinal wall 94. In the embodiment in which suction is used for maintaining the probe on the intestinal wall, the service loop 72 is made sufficiently long that it can remain attached to the suction source until the tip of the endoscope 92 clears the mouth, the anus, or other opening of the digestive tract. After the endoscope clears the body opening, the service loop 72 is clamped so that it maintains an evacuated state in the vacuum lumen 52 between the clamp point and the probe head 40. The service loop 72 is then removed completely from the endoscope 92 and reconnected to a suction device, electronic control equipment or the like (not shown). Once the suction is reactivated, the clamp is released. The probe 40 is then connectable to an electronic unit 120 for acquiring the data.

In the embodiment shown of FIG. 8, the service loop 72 exits the digestive tract through the mouth and passes for connection to the electronic unit. The service loop 72 may be connected by tape to the side of the cheek or the neck of the patient to ensure that the probe is not moved within the digestive tract. The coupling of the probe via a service loop 72 extending through the mouth is useful for short-term monitoring, approximately 1 hour.

Figure 9:
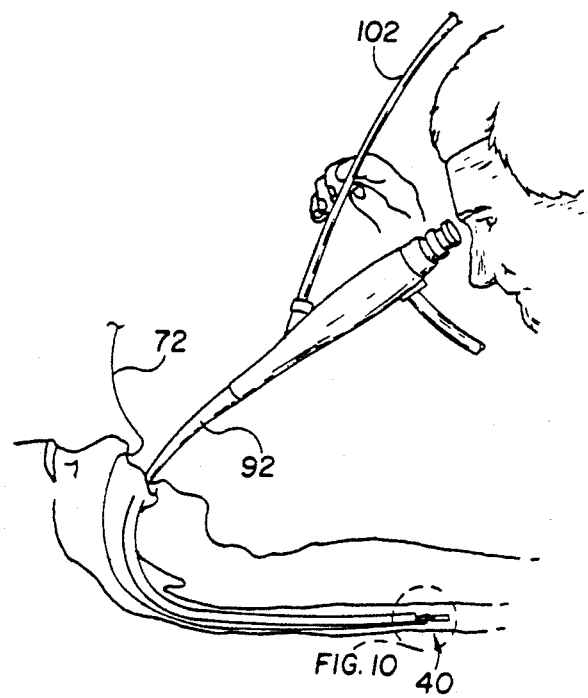
FIG. 9 is a side elevational view of an alternative embodiment of probe placement using an endoscope and having the service loop extend through the nasal passage.
Figure 10:
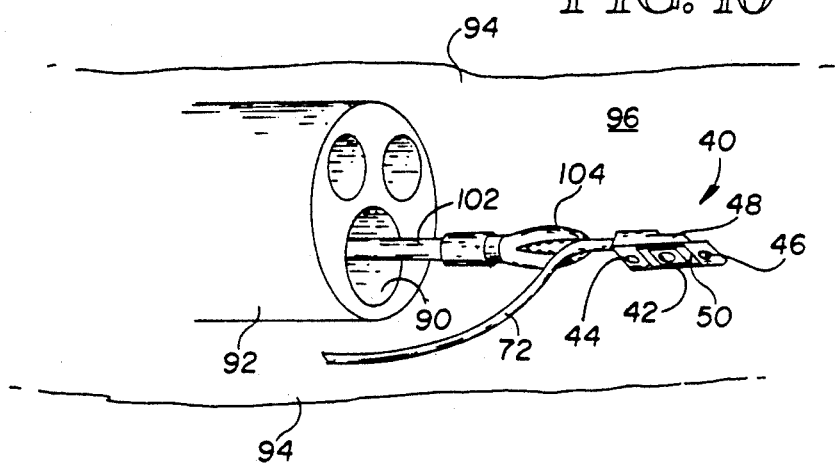
FIG. 10 is an enlarged isometric view of an alternative method of placing the probe within the digestive tract taken from FIG. 9.

For longer-term monitoring, entrance of the service loop 72 through a nasal passage, as illustrated in FIGS. 9 and 10, is preferred. Use of the nasal passage as the entry point to the digestive tract is more tolerable by the patient for longer periods of time. FIG. 9 illustrates an alternative method for carrying the probe 40 into the digestive tract if the point of entry is through the nasal passage. The endoscope 92 is passed through the mouth and into the digestive tract. The service loop 72 having probe 40 coupled to it, is passed through the nasal passage and into the digestive tract. A grasping device, such as a claw 104, coupled to a control rod 102 is passed through the channel 90 to grasp the service loop 72 or probe head 40. The endoscopist guides the placement of the probe 40 onto the intestinal wall 94 and couples it in a manner previously described. After the probe 40 has been properly placed with the grasper 104, the grasper is released and the endoscope is removed from the mouth. The probe wire 54, vacuum lumen 52, and service loop 72 are appropriately connected to the control unit, as previously described. The service loop 72 need not include stiffening rod 100 in the embodiment shown in FIGS. 9 and 10.

FIGS. 8 and 10 illustrate placement of the probe in the inner lumen of the upper gastrointestinal system. The same method illustrated in FIGS. 9 and 10 may be used to place the probe into the lower gastrointestinal system. The endoscope 92 may be of the type that is introducible through the rectum for examination of the lower bowels and large intestine. The wall 94 being examined may be any wall in the digestive tract, such as a wall of the esophagus, the stomach, the duodenum, the large intestine, the colon, the rectum, or any other appropriate wall of the digestive tract or any other organ outside the digestive tract such as the bladder. The probe may also be connected to the outer surface of a gastrointestinal lumen, an organ, or any appropriate region of the body by a similar laparoscope method, surgery or the like.

FIGS. 11 and 12 illustrate the exiting of the service loop 72 from the human body. As illustrated in FIG. 11, the service loop 72 may exit through the nasal passage and be coupled with the appropriate adhesive 106 to the patient for comfort and control. As shown in FIG. 12, the service loop 72 may extend to an ambulatory unit 108. The ambulatory unit 108 is carried by the patient, such as by coupling to the patient with a belt or other technique (not shown). A service loop 72 connected to a probe within the large intestine, extending through the rectum and out the anus, may also be connected to ambulatory unit 108. If placed in an easily accessible region of the body, the transducers may be held in place by hand and attached. Alternatively, they may be placed in "blind" without use of an endoscope.

FIGS. 13-15 illustrate placement of the probe surgically. At the time of surgery, when the skin 108 has been surgically opened, the probe 40 is attachable to the outer wall of the intestine 94 or to some other organ often by the hand of the physician. The service loop 72, coupled to the probe 40 or a plurality of probes 40, arranged either in series or parallel, is brought out of the surgical opening. After the incision has been closed, the service loop 72, including the electrical coupling wires 54-58, is attachable to an electronic ambulatory unit, as best illustrated in FIG. 15. The service loop 72 may be brought out through the closed suture site along the side of a drainage tube or directly through a region of the closed wound.

The enlarged embodiment of FIG. 14 illustrates an advantageous placement of the probes in series along a wall of the intestinal tract. Some types of surgery require incisions into the intestinal tract. Surgical removal of an entire section of the intestinal tract and the coupling of the intestinal walls together with suture is sometimes performed. One usage of the system permits the monitoring of the intestinal recovery of a surgical anastomosis of the intestine. For example, the probes 40 may be placed in series along either side of the anastomosis. The outputs from the individual probes may be compared with each other to determine when the intestine is properly healed and beginning to function. Monitoring movement of one portion of the intestinal wall relative to another portion following surgery provides valuable information regarding the healing status and functioning of the intestine.

Figure 16:
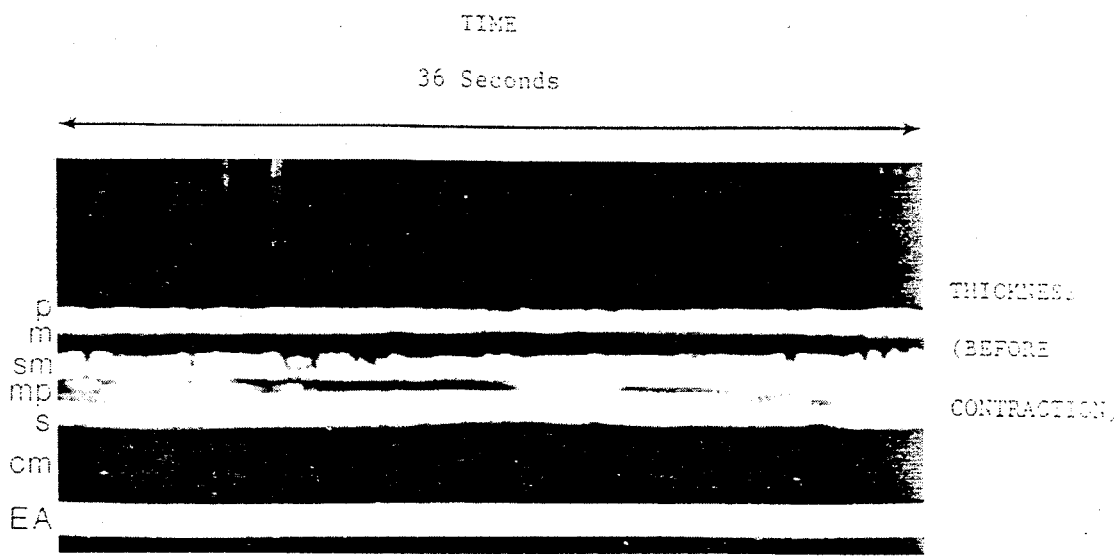
FIG. 16 is a plot of the reflections from a wall of the digestive tract while at rest.
Figure 17:
FIG. 17 is a plot of the reflections from the wall region of FIG. 16 during a contraction.

FIGS. 16-17 are plots generated from the output of the ultrasonic transducer 42. The plots of FIGS. 16 and 17 are M-mode plots of a pig's stomach at laparotomy. In the embodiment of FIG. 16, the probe 40 was surgically coupled to the outer wall of the pig's stomach by suturing.

The plots of FIGS. 16 and 17 are from a fixed location of the transducer 42 over time, the ordinate representing depth into the wall and the abscissa representing time. The brightness represents the intensity of the echo received. Individual layers of the wall over time are therefore observable. Several times a second a pulse is generated by the transducer. A scan line is plotted for each pulse generated, the echoes received from each layer being on a single scan line for each pulse. The plots of FIGS. 16 and 17 were made over 36 seconds, a plurality of scan lines being compiled from the received ultrasonic energy for the respective pulses over the period of time to make the plots.

In the M-mode image of FIG. 16, the intestinal wall 94 is shown without a contraction. The individual layers of the intestinal wall can be seen. The initial reflection "EA" is the excitation artifact. "cm" represents the coupling media. The outer layer, the serosa "s" of the intestine, is distinguishable from the muscularis propria "mp," the submucosa "sm," and the mucosa "m." A highly reflective layer of paraffin "p" was placed against the mucosa for support in this trial, along the inner wall of the stomach. The paraffin layer would not be present in clinical use. For the 36-second time period of FIG. 16, the wall of the stomach did not significantly change shape and each layer remained approximately the same thickness.

FIG. 17 is an M-mode plot of the same region of the stomach as FIG. 16 during a contraction over a 36-second period. A contraction of the stomach was induced with a nerve stimulator. Thickening of the intestinal wall is evident. An increased thickness of approximately 23% is measurable. The increase was caused by changes in the muscle thickness because the mucosa and submucosa did not change in thickness. The mucosa, submucosa, and other regions each appeared as a continuous layer over time when there was no contraction.

The M-mode, high-frequency, ultrasonic imaging shows promise as an apparatus and method for assessing gastrointestinal muscle contraction and relaxation. During a contraction, the muscularis propria ("mp") is split in some specimens into two layers by a very thin, highly reflective collagen layer which permits identification of the circular and longitudinal muscle layers in those specimens. A comparison between the high-resolution, ultrasonic M-mode image of the isolated strips of the wall with simultaneous measurement of length and tension is possible. Relaxation of the circular muscle appears to result in thinning of the circular muscle layer to its baseline appearance, as illustrated in FIG. 16. The technique may also permit simultaneous assessment of circular and longitudinal muscle activity.

The image may also be displayed using a "fused method," of display which permits a significant increase in the vertical sampling resolution. According to the fused method, information from two different pulses is combined to form a single vertical scan line in the image. In a standard video format having a scan rate of about 30 times a second, a single scan line is produced every 62.5 microseconds. However, the intestinal wall is sufficiently thin that all echoes from layers of interest have returned after less than 30 microseconds. If all of the returned data is displayed at the rate it is received, only half a scan line is filled. According to the fused method, the transducer is pulsed at twice the rate required to produce a single scan line, once every 31.25 microseconds, in the standard video format. The data from the first pulse is applied to every other pixel in a single scan and the data from the second pulse is applied to every other pixel in the same scan line, offset one pixel from the data of the first pulse. The data from the first and second pulses are thus interdigitated to fill every pixel in a single scan line. Each scan line contains data from two pulses similarly interdigitated. Detection of individual layers and edges of each layer is enhanced using the fused method.

Figure 18:
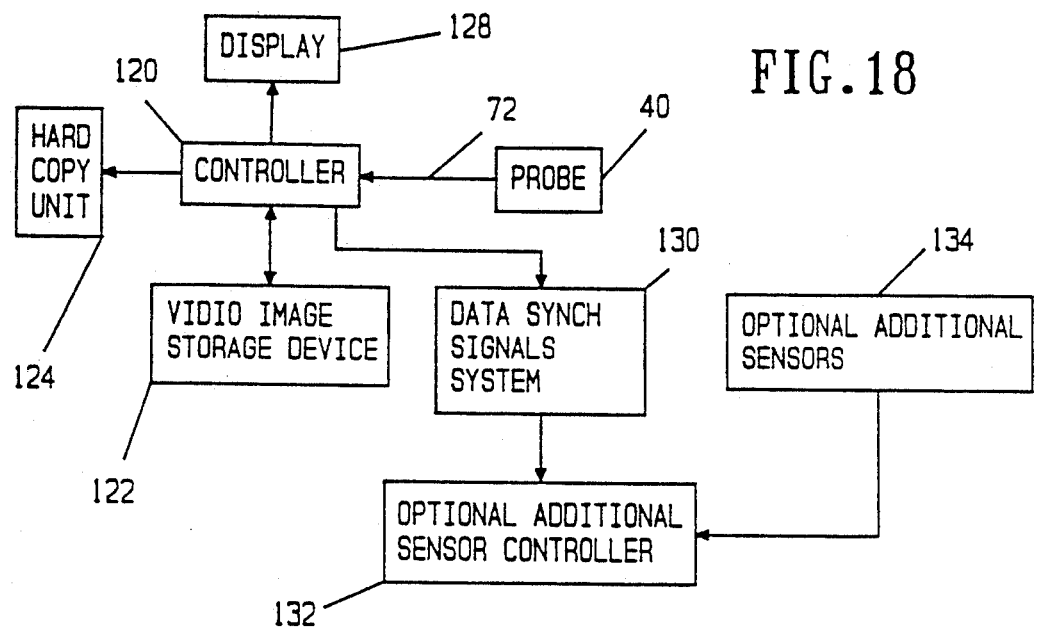
FIG. 18 is a block diagram of a clinical data acquisition and analysis system.
Figure 19:
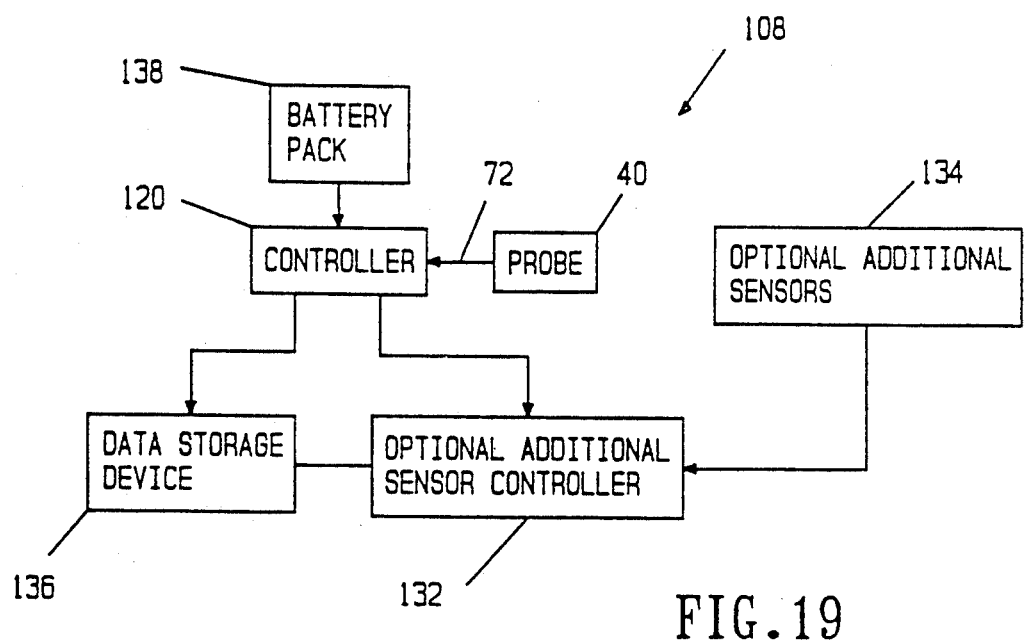
FIG. 19 is a block diagram of an ambulatory data acquisition system.

Two embodiments of a data acquisition system are illustrated in FIGS. 18 and 19, respectively. The clinical system of FIG. 18 allows analysis of the data to be made simultaneously with the collection of the data using the same system. The display aids significantly in placing the probes and allowing confirmation that the probes are producing high-quality ultrasonic images and that adequate data are acquired.

A multichannel, high-resolution, ultrasonic M-mode controller 120 controls the basic operation of the device. The controller 120 is coupled via the service loop 72 to the probes 40 positioned within the patient. The controller 120 interacts with the ultrasonic transducers located in the probe: exciting them to send ultrasonic energy, receiving the reflected energy, and amplifying and processing it to produce an M-mode image of the intestinal wall. The output of the controller 120 is coupled to a display 128, a video storage device 122, and a hard-copy plotting device 124, such as that used to produce the plots of FIGS. 16 and 17. A physiological controller 132 receives input from physiological sensors 44, 46, 60, and 64 in the probe 40, which is coupled to the subject. Alternatively, the controller 132 may be coupled to other physiological devices 134 at a location other than on the probe 40, such as a conventional EKG sensor, blood pressure sensor and the like. A data synchronization system 130 is coupled between a physiological functions controller 132 and the multichannel ultrasonic controller 120. The data synchronization system 130 permits correlation between the ultrasonic data and other physiological data as collected from sensors 134 or the probe 40. The controller is shown and described in more detail with respect to FIG. 20. A method is therefore provided for recording and observing other data for the purpose of correlating time events with the ultrasonic M-mode image of motility action.

FIG. 19 illustrates an ambulatory unit 108 which is a scaled-down version of the clinical unit 118. The ambulatory unit 108 includes the features necessary to acquire data over a long period of time. Analysis is performed later with a secondary device. The purpose of the ambulatory unit 108 is to monitor and record motility action for a long enough time, perhaps 8 to 24 hours or more, to capture the occurrence of motility disorders that may occur in various short episodes at random times or at times when the patient is not in the clinic. The ambulatory unit 108 includes a multichannel ultrasonic controller 120 directly coupled to the probes 40 to generate the signals to produce the electronic energy, receive the energy, process it, and place it into a form suitable for storage in the data storage device 136. The storage device may be any one of a variety of mass storage devices presently available, such as a mini-video recorder, a compact laser disk device, a magnetic tape cassette recorder, a large block of solid-state memory, or the like. A battery pack 138 is included in the ambulatory unit 108 for providing power to the system. The ambulatory unit 108 may also include a controller 132 for other physiological signals and additional sensors located within the probe 40 or otherwise coupled to the patient, if desired.

Figure 21:
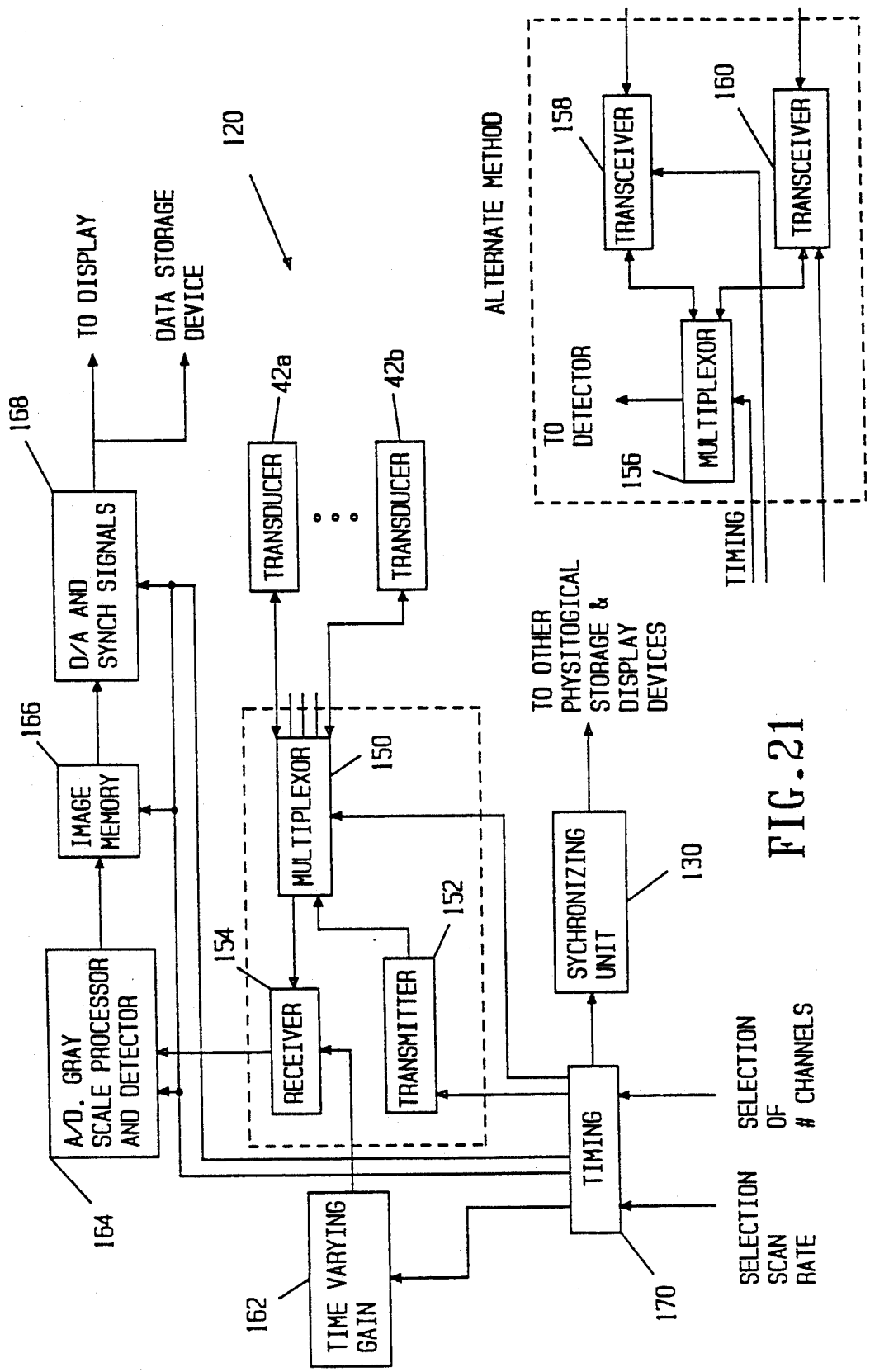
FIG. 21 is a block diagram of a multichannel, data acquisition system.

FIG. 21 illustrates in detail an embodiment of the components of the multichannel, high-resolution, ultrasonic M-mode controller 120 shown in FIG. 18. The controller 120 is capable of controlling a plurality of ultrasonic transducers 42a-42n. The controller 120 applies the electrical signal to excite them and receives the signal representative of reflected ultrasonic energy from them.

The controller 120 need not necessarily be multichannel throughout. A multiplexer 150 may be used for time sequential pulsing and acquiring of data from each of the transducers 42a-42n. The signal may then be passed to single-channel, image-forming circuitry. In a first embodiment, the multiplexer 150 is of a low-noise type with a sufficient power rating to pass the high-power transmission energy from the transmitter 152 and pass the received signal from the transducers, with little degradation, to the receiver 154.

In an alternative embodiment, the transmitter is directly coupled to the transducers 42a-42n or through the transceivers 158-160, if desired. The high-excitation voltage required for the transducers to emit ultrasonic energy does not pass through the multiplexer. A multiplexer 156, having less stringent requirements, receives the output from respective transceivers 158 and 160. The received signal may be a low-power signal, and the transceivers 158 and 160 have adjusted the signal to a level for use with the multiplexer. In the alternative embodiment, the multiplexer needs to be designed to tolerate only the voltage levels of the signals at the output of the transceivers and need not tolerate the high-voltage levels generated by the transmitter for the transmission of ultrasonic energy.

A conventional time-varying gain control circuit 162 is usable with the receiver 154 or the transceivers 158 and 160 to vary the gain of the reflected signal to compensate for attenuation of ultrasound energy that has traveled farther through the tissue. The gain of the received signal is adjusted based on timing of the received reflection to ensure that the intensity of the signal is proportional to the reflectiveness of the layer within the wall, independent of the depth within the wall. Because the ultrasonic energy attenuates as it travels deeper into the wall, the use of a time-varying gain control circuit 162 compensates for attenuation due to depth. A plurality of gain control circuits 162 may be used, one for each transceiver 158 and 160, if desired.

The output of the receiver 154, or multiplexer 156, if desired, may be applied to a conventional gray scale processor and detector 164. The gray scale processor includes an automatic gain control circuit of a type well known in the industry. The average value of the signal is maintained within a selected range. If the average value is too low, the signal gain is increased. If the average value is too high, the gain is lowered to maintain the signal average within the selected range. Circuits able to provide this type of automatic level control are well known in the video industry. Placing a gray scale processor in the first processing section 164 permits processing the amplitude of the signal to allow both high- and low-level echoes to be recorded so that they both appear in an image. The detector converts the envelope of the alternating radio frequency signal that corresponds to the reflected ultrasonic signal into the working signal for the est of the system.

The image memory storage device 166 acquires analog data line by line, storing it in order to produce a complete image. A standard videotape recorder is suitable for high density storage at each scan line. Each line represents a B-mode line of the echoes that return from the tissue in response to the transmission of a burst of ultrasonic energy into the tissue as initiated by the transmitter. Once a complete image block of data is acquired, the block of data may be recorded and a hard-copy plot produced for that period of time. Alternatively, newly acquired data may be written into and over the oldest data, line by line. Writing over the oldest data line by line produces a continuously updated M-mode display. The output of the image memory device 166 is coupled to the digital-to-analog converter and signal-synchronizing circuit 168. Coupling of the image memory circuit 166 allows the images to be recorded on standard analog video recorders and disks as well as displayed on standard video monitors. The signal can pass from the digital-to-analog stage 168 to be recorded in digital form on a mass digital data storage device, if desired.

The timing controller 170 provides timing control for the entire system. The timing controller 170 activates the timing for the transmitter 152, or transceivers 158 and 160, if used. The timing controller 170 also controls the timing in the multiplexer 150, activation of the time-varying gain, control of the gray scale processor 164, image memory device 166, digital-to-analog converter 168, and to the synchronizing unit 130 for the controller 132 for other physiological data, as previously described with respect to FIGS. 18 and 19. The synchronization unit 130 may include a multiplex or microprocessor to permit time correlation between the ultrasonic data and other data.

An operator sets a number of channels, depending upon the number of transducers to be monitored, and also selects a scanning rate. The scanning rate determines the time resolution of the M-mode system. The scan rate is the time required to generate one full image. In FIGS. 16 and 17 a scanning rate of 36 seconds was used. The repetition rate is the rate at which each individual transducer is pulsed. For FIGS. 16 and 17, assuming that the image includes 512 vertical scan lines, the repetition rate is approximately 14.2 times a second. For a standard video image, the repetition rate is approximately 1600 times per second and the scan rate is about 30 times per second. Because the contractions of the digestive tract occur over many seconds to perhaps minutes, the scanning rate is widely adjustable. A further feature of the system is that the repetition rate of the transducer excitation is controllable by the scanning rate. If a lower scanning rate is used, the repetition rate of the transmitter is lowered to avoid overexposing the subject to ultrasonic energy. Therefore, the transmission of energy is confined to a rate that will properly produce the individual scan lines in an image but not be sufficiently high to cause damage to the patient.

The scanning rates of obtaining the data, storing the data, and viewing the data are variable and independent of each other. Each scan rate may be any value in the range of 1 to 2 hours or as short as 15 seconds, if desired. In one embodiment, the scan rate of obtaining and storing data is a preselected rate and the scan rate of displaying the data is variable over a wide range of values to provide the rapid data-reading device 140 shown in FIG. 20. The repetition rate is set at some high value, such as 1600 times per second. Data for each scan line is stored on a video tape, for example, 1600 scan lines per second, for each transducer in the body. To display in the rapid reading mode, each scan line is not displayed. Rather, only scan lines separated by a predetermined number of scan lines are displayed to produce an image. For example, each displayed scan line may correspond to pulses separated by 5 seconds, producing a scan rate of approximately 45 minutes for a 512-horizontal pixel display. Two hours of data is then viewable in three images. The movement of the intestinal wall is sufficiently slow that significant movement will be seen using a display rate of one line per five second time interval. If one time period is of particular interest, the stored data may be reread, this time displaying at a different scan rate, such as from two scan lines per second to provide a scan rate of approximately 4.2 minutes. Each image thus represents 4.2 minutes in real time. The image display rate may be raised to approximately 15 times per second to produce a 36 second scan rate as shown in FIGS. 16 and 17. The density of stored scan lines used to produce an image is variable up to the repetition rate of the transducer. For example, data from each pulse may be displayed, at the repetition rate of 1600 times per second, for each transducer, to obtain a frame representing 1/30 of a second time elapsed, if desired. If using the fused method, the repetition rate doubles for a given scan rate. The repetition rate is selected based on the need for data and data storage capabilities generally in the range of once per second up to several hundred times per second. The rate is selected to minimize the energy propagated into the patient and yet provide sufficient data for the expected movement to be monitored.

The data from a plurality of different probes 40 are grouped together so that multiple M-mode images appear aligned in time in the display and in hard copies so that timing of the contractions through different regions may be easily compared and correlated.

Figure 20:
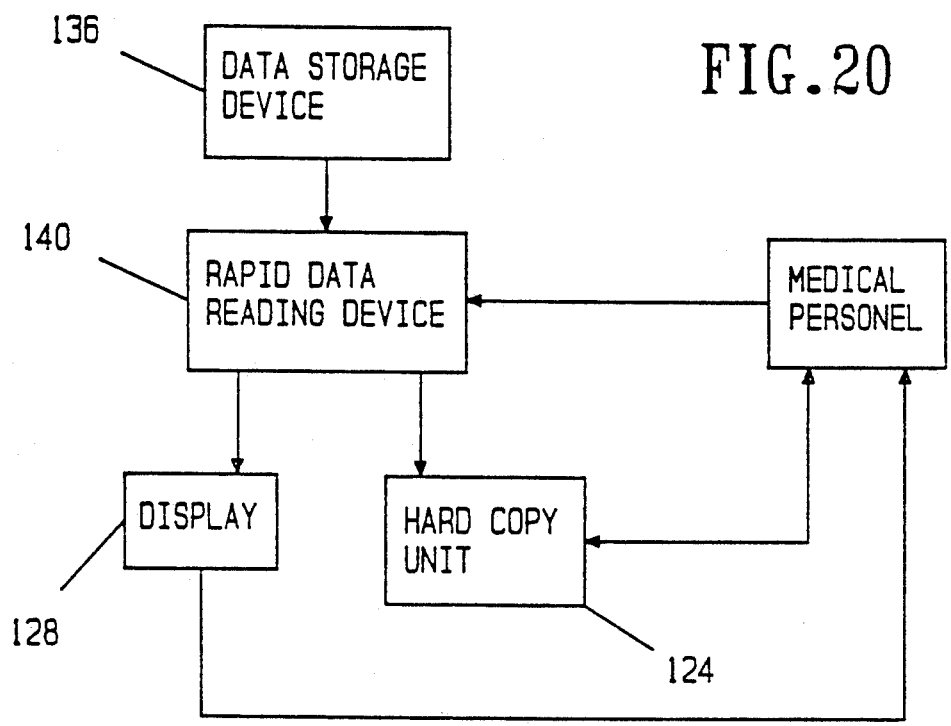
FIG. 20 is a bock diagram of a data analysis system.

FIG. 20 is a block diagram of a data analysis system for use with data collected by the ambulatory device 108. Because many hours of data may be recorded in the ambulatory analysis unit 108, the analysis system is designed to permit a readback at a rate many times the recording rate. Long periods of time in which no activity of interest occurred may be rapidly passed over. The data analysis system therefore includes a rapid data-reading device 140 which is coupleable to the data storage device 136 of the ambulatory unit 108.

The outputs of the rapid reading device 140 are connected to a display 128 and also to a hard-copy unit 124 to permit copies to be made of regions of interest. Medical personnel operating the rapid reading device and monitoring the hard copy and visual display operate the system to provide analysis of the data and make the diagnosis. When a region of interest is located, it may be studied at a lower speed or even in "pause" mode.

Following the testing, the probes are removed. The method of removal depends upon the design and style of the probe as well as the method of placement. In the event a suction attachment is used for placement, the suction is disengaged and the probes withdrawn by tugging on the connection lead or service loop 72. In some embodiments, air pressure may be applied through the suction lumen to release the probe initially attached by suction to ensure proper release. In other embodiments, a special release device may be included that is activated to release the probe from the intestine and permit it to be withdrawn. In the embodiments in which the probes are mechanically attached, such as by glue or suture, the substance may be made biodegradable and automatically release the probes after a period of time. The probe is removable by tugging on the connection lead after it is loose. For surgically implanted probes, it may be necessary to surgically remove the suture and remove the probe. Biodegradable sutures can be used so as to avoid the need for surgical removal.

We claim:

1. An apparatus for simultaneously measuring thickness of a wall of the digestive tract and the local pressure within the digestive tract of a living body, comprising:
   an ultrasonic transducer within a probe that is adapted to be attached in a fixed position to said wall within said living body;
   a transmitter means for causing said transducer to emit a plurality of ultrasonic pulses into said wall at a selected rate;
   a receiver means for receiving electronic signals from said transducer corresponding to ultrasonic energy reflected from said wall, the round trip time for the ultrasonic energy reflected from said wall being indicative of the thickness of the wall for the reflected ultrasonic energy;

a pressure sensor means adjacent said transducer for measuring the gas pressure in said digestive tract simultaneously with said transducer transmitting ultrasonic energy into walls of said digestive tract;

a flexible coupling means connecting said transmitter means to said transducer for permitting said transducer to move freely with respect to said transmitter means to permit movement of said wall to which said transducer is adapted to be attached; and a display means for displaying said received electronic signals.

2. The apparatus according to claim 1, further including a plurality of said probes having respective transducers spaced from each other when attached along said lumen wall, said transmitter means causing each transducer within said probes to emit ultrasonic energy, and said display means providing an individual display for signals received by each of said transducers.

3. The apparatus according to claim 1 wherein said transmitter means emits said ultrasonic pulses at a preselected repetition rate over a period greater than one hour and said display means provides a printed record of reflections from said pulses over said period.

4. The apparatus according to claim 1 wherein said pressure sensor is within said probe.

5. An apparatus for measuring thickness of a wall of the digestive tract of a living body, comprising:

an ultrasonic transducer within a probe that is adapted to be attached in a fixed position to said wall of the digestive tract;

a transmitter means for causing said transducer to emit a plurality of ultrasonic pulses into said wall at a selected rate;

a receiver means for receiving electronic signals from said transducer corresponding to ultrasonic energy reflected from said wall, the round trip time for the ultrasonic energy reflected from said wall being indicative of the thickness of the wall for the reflected ultrasonic energy;

a muscle tension sensor means adjacent said transducer for measuring the tension in said muscle adjacent to said transducer;

a flexible coupling means connecting said transmitter means to said transducer for permitting said transducer to move freely with respect to said transmitter means to permit movement of said wall to which said transducer is adapted to be attached; and a display means for displaying said received electronic signals.

6. An apparatus for measuring movement of a portion of a living body comprising:

an ultrasonic transducer within a probe that is adapted to be attached in a fixed position to said living body;

a transmitter means for causing said transducer to emit a plurality of ultrasonic pulses into said living body at a selected along a given scan line direction rate;

a receiver means for receiving electronic signals from said transducer corresponding to ultrasonic energy reflected from within said body;

a data storage means for storing data corresponding to said electronic signals, said data being stored in scan lines, one scan line storing data for each pulse transmitted, the stored data being representative of movement of a portion of the living body;

a variable data reading means for reading only said scan lines which are temporally separate from each other by a predetermined variable number of scan lines;

a display means for displaying said scan lines which have been read by said variable data reading means.

7. The apparatus according to claim 6 wherein said number is fifty.

8. The apparatus according to claim 6 wherein said number is ten.

9. The method of studying movement of a wall within a living body, comprising:

attaching a plurality of ultrasonic transducer probes to said wall within said living body, said transducer probes being spaced from each other along said wall of said living body;

coupling the plurality of probes to each other with a flexible coupling, each of the probes including an ultrasonic transducer;

transmitting ultrasonic energy into said wall at a selected frequency for each of said probes within the plurality of probes;

receiving ultrasonic energy reflected from individual regions within said wall, by each probe of said plurality, said frequency being selected to image individual regions within said wall;

repeating said transmitting and receiving steps a plurality of times over a selected interval of time; and producing a plot of individual regions within said wall over time based on the ultrasonic energy reflected from said individual regions over time, at which each probe within said plurality of probes is positioned.

10. The apparatus according to claim 9, further including a data storage means for storing data corresponding to said electronic signals, said data being stored in scan lines, one scan line storing data from two pluses, the data from the pulses being interdigitated in the scan line.

11. The method according to claim 9, further including the steps of:

coupling a plurality of probes to each other with a flexible coupling, each of said probes including an ultrasonic transducer;

attaching said plurality of transducer probes to said wall, said probes being spaced from each other along said wall;

repeating said transmitting and said receiving steps for said plurality of transducers; and producing individual plots for each transducer over time.

12. The method according to claim 9 wherein said wall is a wall of the digestive tract within a living body, and further including the steps of:

placing some food within said digestive tract; and repeating said transmitting and receiving step while said food is being digested.

13. The method according to claim 9 wherein said wall is the wall of a lumen within the human body, further including the step of measuring the local pressure within said lumen simultaneously with performing said transmitting and receiving steps.

14. An apparatus for determining the motility of a region of a living body, comprising:

a plurality of probes, each having an ultrasonic transducer, said probes being adapted to be attached to said region;

a transmitter means for providing an electrical signal to said transducers, causing them to emit an ultrasonic pulse;

a receiver means for receiving electrical signals from said transducers representative of the ultrasonic energy reflected from said region;

a multiplexer means for selectively coupling said transmitter means to one of said plurality of said transducers;

a plotting means for producing a line in a plot corresponding to the received signals;

a line selection means coupled to said plotting means for selectively providing to said plotting means some of said received signals, and blocking some of said signals from said plotting means, such that said plot includes lines for some of said received signals and does not include lines for other of said received signals; and a clock means coupled to said transmitter means for causing said transmitter means to emit said electrical signals at selected intervals.

15. The apparatus according to claim 14 wherein said probes are coupled to each other with a flexible coupling to permit said transducers to freely move relative to each other as said region of the living body moves.

16. The apparatus according to claim 14 wherein said line selection means includes means for causing every other one of said lines to be plotted and every other one of said lines to be blocked and not be plotted in said plot.

17. The apparatus according to claim 14 wherein said line selection means includes means for providing every tenth line to said plotting means and blocks nine out of ten lines from entering said plotting means.

18. The apparatus according to claim 14 wherein said selection means includes a video display monitor.

19. A method of simultaneously measuring movement of walls of the digestive tract within an esophagus and within a large intestine of a living body comprising:

attaching an ultrasonic transducer probe to a wall of said digestive tract within said esophagus;

attaching an ultrasonic transducer probe to a wall of said digestive tract within said intestine;

simultaneously transmitting ultrasonic energy into said esophagus wall and said intestine wall via respective transducers;

receiving the transmitted ultrasonic energy that is reflected back from the esophagus wall and the intestine wall respective via respective transducers;

repeating said transmitting and receiving steps a plurality of times over a selected interval of time; and producing a plot of the change in thickness of regions within said respective walls over time based on the ultrasonic energy reflected from said regions over time.

20. The method of studying movement of a wall within a lumen of a living body, comprising:

attaching an ultrasonic transducer probe to said wall within said living body;

transmitting ultrasonic energy into said wall;

receiving ultrasonic energy reflected from regions within said wall;

repeating said transmitting and receiving steps a plurality of times over a selected interval of time;

producing a plot of regions within said wall over time based on the ultrasonic energy reflected from said regions over time; and measuring the local pressure within said lumen simultaneously with performing said transmitting and receiving steps.

21. The method of studying movement of a wall within a living body, comprising:

attaching an ultrasonic transducer probe to said wall within said living body using a rigid rod coupled to said probe, said transducer probe being connected to a control circuit with a coupling member;

removing said rigid rod from being coupled to said transducer probe after said transducer probe is attached to said wall to render said coupling flexible between said transducer probe and said control circuit;

transmitting ultrasonic energy into said wall;

receiving ultrasonic energy reflected from regions within said wall;

repeating said transmitting and receiving steps a plurality of times over a selected interval of time; and producing a plot of regions within said wall over time based on the ultrasonic energy reflected from said regions over time.

* * * * *

UNITED STATES PATENT AND TRADEMARK OFFICE
CERTIFICATE OF CORRECTION

PATENT NO. : 5,247,938
DATED : September 28, 1993
INVENTOR(S) : Fred E. Silverstein et al.

It is certified that error appears in the above-indentified patent and that said Letters Patent is hereby corrected as shown below:

In claim 6, column 13, line 61, after "selected" and before "along", please insert --rate--.

In claim 6, column 13, line 62, please delete "rate".

In claim 6, column 16, line 6, please delete "respective" and substitute therefor --respectively--.

Signed and Sealed this

Thirty-first Day of May, 1994

*Attest:*

BRUCE LEHMAN

*Attesting Officer*  *Commissioner of Patents and Trademarks*